United States Patent [19]
Focelle et al.

[11] Patent Number: 4,966,603
[45] Date of Patent: Oct. 30, 1990

[54] ANEURYSM CLIP

[75] Inventors: Dennis M. Focelle, Minneapolis; Terrance W. Hanlon, Blaine, both of Minn.

[73] Assignee: RMS Company, Minneapolis, Minn.

[21] Appl. No.: 384,124

[22] Filed: Jul. 24, 1989

[51] Int. Cl.⁵ .............................................. A61B 17/12
[52] U.S. Cl. ....................................... 606/158; 24/945
[58] Field of Search .................. 606/157, 158; 24/509, 24/499, 547, 551, 552, 563, 545, 546

[56] References Cited

U.S. PATENT DOCUMENTS

| | | |
|---|---|---|
| 2,215,725 | 7/1939 | Martinson . |
| 3,827,438 | 8/1974 | Kees, Jr. . |
| 4,024,868 | 5/1977 | Williams . |
| 4,360,023 | 11/1982 | Sugita et al. . |
| 4,484,581 | 11/1984 | Martin et al. . |
| 4,777,949 | 10/1988 | Perlin .................................. 606/158 |
| 4,796,625 | 1/1989 | Kees .................................... 606/158 |

Primary Examiner—Michael H. Thaler
Attorney, Agent, or Firm—Peterson, Wicks, Nemer & Kamrath

[57] ABSTRACT

The one-piece aneurysm clip is fabricated from a predetermined length of round metallic rod or wire. The clip includes a pair of cooperable jaw portions and a coil portion that supplies a closing force to the jaws, doing so through first and second connecting portions. The first connecting portion has a longitudinal slot formed therein and the second connecting portion is U-shaped having a thickness correlated with the width of the slot so that the jaw portions are maintained in alignment. The degree of closing force supplied by the coil is determined by the width and depth of a slot formed in a segment thereof.

4 Claims, 1 Drawing Sheet

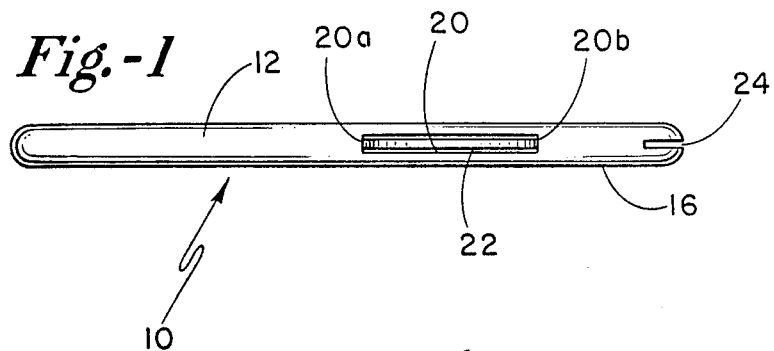
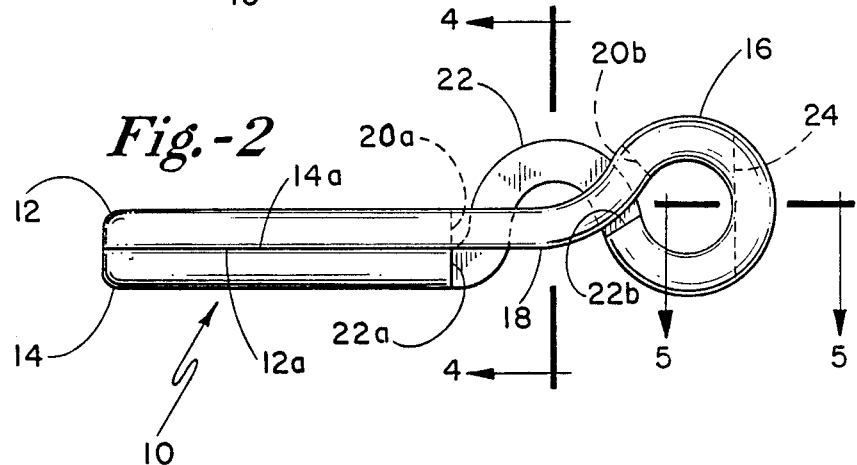
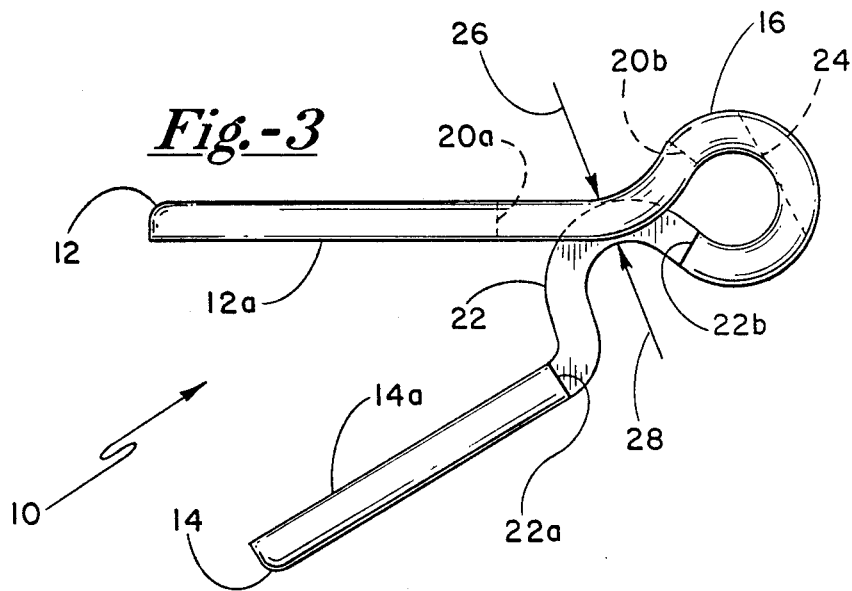
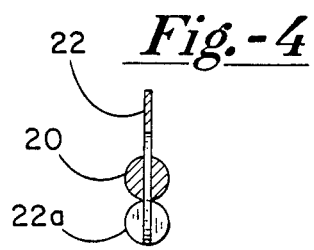
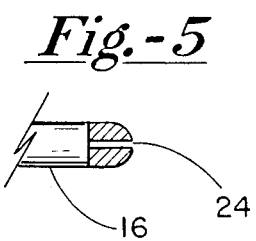

ANEURYSM CLIP

BACKGROUND OF THE INVENTION

1. Field of the Invention

This invention relates generally to aneurysm clips, and pertains more particularly to a one-piece clip in which lateral movement of the clip's jaws is prevented.

2. Description of the Prior Art

Maintaining jaw alignment has been a problem in the design of aneurysm clips, the problem being quite significant by reason of the miniaturized dimensions (on the order of only 0.75 inch in overall length) of such clips.

The problem has been recognized in U.S. Pat. No. 4,484,581 issued on Nov. 27, 1984 to Fritz Martin et al. Functionally, the patented clip construction serves its purpose by employing a guide plate at one side of a recess in which a portion of a cross-piece moves. However, because of the small size of an aneurysm clip, this clip is relatively costly to manufacture.

Although intended for use in embalming, the clamp described in U.S. Pat. No. 2,215,725 issued on Sept. 24, 1940 to Raymond W. Martinson is of general structural interest. In this situation, it is really the width of the strip metal that prevents lateral misalignment. Assisting in this realization is the fact that one jaw moves within a slot in a second jaw, but the curved jaws must be separated to such an extent that the one jaw is completely out of the slot in the other jaw in order to receive therein an artery or a vein of a dead body.

SUMMARY OF THE INVENTION

Accordingly, an important object of our invention is to provide an aneurysm clip that incorporates therein a positive jaw alignment, doing so in a simplified fashion so that the clip can be fabricated at a relatively low cost. In this regard, it is an aim of the invention to provide a clip of one-piece construction which obviates the necessity of assembling any individual parts and at the same time preventing a possible disassembly of the clip, either during or after being used.

Another object of the invention is to provide an aneurysm clip of the foregoing character that cannot be overstressed in use. More specifically, owing to the miniaturized size of aneurysm clips, it is necessary to utilize a forceps-type tool to actuate the jaws into an open or artery-receiving position, and when such an implement is employed our invention makes it impossible to apply a sufficient amount of force in the opening procedure that would exceed the elastic limit of the metal of which our clip is fabricated.

Briefly, our invention envisages a one-piece aneurysm clip that is fabricated from a predetermined length of rod or wire stock. The clip, when completed, has a pair of cooperable jaws, these jaws being biased into a closed or artery-gripping relationship by means of an appropriately formed integral coil. The jaws are connected to the coil by means of a first connecting portion having a slot formed therein providing a constrained or guided movement for a U-shaped or humped connecting portion associated with the other jaw. In opening the jaws with a forceps-type implement, the U-shaped connecting portion moves within the slot in the first-mentioned connecting portion but the movement of this U-shaped portion is limited so that overstressing is avoided, such a condition being realized when the bight of the U-shaped portion is fully received or nested in the slot of the first connecting portion. The degree of clamping action applied to the jaws is governed by a slot formed in the resilient coil, the size of the slot determining the degree of resilient force applied to the jaws and thus influencing the amount of pressure exerted on the clamped artery or vein.

BRIEF DESCRIPTION OF THE DRAWING

FIG. 1 is a top plan view of an aneurysm clip exemplifying our invention;

FIG. 2 is an elevational view of the clip with the jaws closed;

FIG. 3 is an elevational view with the jaw open, a pair of arrows indicating the opening force that is applied through the agency of a forceps-like implement;

FIG. 4 is a sectional detail taken in the direction of line 4—4 of FIG. 2; and

FIG. 5 is a fragmentary sectional view taken in the direction of line 5—5.

DESCRIPTION OF THE PREFERRED EMBODIMENT

Referring now to the drawing, our one-piece aneurysm clip has been denoted generally by the reference numeral 10. The clip 10 includes a pair of cooperable jaws 12 and 14, the jaw 12 having a clamping surface 12a and the jaw 14 a similar surface 14a; the surfaces 12a, 14a are knurled or serrated so as to enhance their retentive capability when gripping an artery or vein.

The way in which the jaws 12 and 14 are urged or biased toward each other is by means of a resilient coil 16. A portion 18 connects the jaw 12 to one end of the coil 16, the connecting portion 18 having a longitudinal slot 20 formed therein with the ends of the slot being labeled 20a and 20b. A second portion 22 connects the jaw 14 to the other end of the coil 16. The portion 22 is U-shaped, actually in the form of a hump, as can be appreciated from FIG. 2. As can be understood from FIGS. 1 and 4, however, the U-shaped connecting portion 22 is relatively thin, thin enough so that it moves freely within the slot 20. Since the sides of the slot 20 guide and constrain the portion 22 from lateral movement, it follows that the width of the slot 20 should be only slightly greater than the width of the U-shaped portion 22. The U-shaped portion 22 has one end connected to the jaw 14, as already indicated, forming shoulders 22a at either side thereof as best understood from FIG. 4. The other end of the U-shaped portion 22 is connected to the coil 16, forming a shoulder 22b at each side thereof.

A feature of the invention is that the degree of closing force applied to the jaws 12 and 14 can be determined by the width and depth of a slot 24 formed in a segment of the coil 16. The wider the slot 24 and the deeper the slot 24 is, the less closing force is exerted on the jaws 12, 14 by the coil 16.

Obviously, to open the jaws 12 and 14, a sufficient amount of force must be applied to overcome the biasing action of the coil 16. FIG. 3 depicts our clip in its open position. The way in which the clip 10 is opened is by applying a sufficient amount of force between the bight of the connecting portion 22 and the middle of the connecting portion 18. This is done by means of a forceps-like tool or implement which need not be illustrated. In lieu of illustrating the actual implement, the force applied to the bight of the portion 22 is represented by an arrow 26, whereas the opposing force applied to the portion 18 is represented by the arrow 28.

What should be understood is that when an implement engages the portions 22 and 18, as indicated by the arrows 26 and 28, the bight of the U-shaped portion 22 cannot move beyond the condition illustrated in FIG. 3 because the bight is then fully received or nested in the slot 22. In other words, the forceps-like implement cannot force the U-shaped portion 22 farther because such action is prevented by one of the jaws of the implement engaging the upper side of the connecting portion 18. Likewise, the other jaw of the implement, which is applied to the underside of the bight belonging to the U-shaped portion 22, cannot cause the U-shaped portion to move farther upwardly because the movement of the second implement jaw is prevented when it engages the underside of the connecting portion 18. Such a state of affairs is reached before the elastic limit of the clip 10 is exceeded; in other words our clip 10 cannot be overstressed. As will presently be better understood, the thickness or vertical dimension of the portions 18 and 22 are equal because the aneurysm clip 10 is fabricated from a single length of round metallic rod or wire stock.

It may be of assistance in fully appreciating the benefits to be derived from a practicing of our invention to describe briefly the manner in which the aneurysm clip 10 is fabricated. In this regard, a section or length of round metallic rod or wire is cut to the appropriate length so that when bent into the configuration of FIG. 2, the jaws 12 and 14 will abut or engage each other. It is not believed necessary to show the pre-cut length of wire stock; however, when still in its straightline configuration, the serrated or knurled surfaces 12a and 14a are cold formed on what are to constitute the jaws 12 and 14. Also, while the wire stock is still straight, the slot 20 is formed, such as by means of an electrical discharge machine (EDM). It is then that the U-shaped portion 22 is cold formed while the wire stock is still round. As previously explained, the U-shaped portion 22 is relatively thin, so after providing the desired radius to the U-shaped or humped portion 22, its thickness is reduced by cold forming, milling, grinding or EDM. Next, the coil 16 is formed by appropriate bending. It is then that the thinned down U-shaped portion 22 is forced upwardly through the slot 20.

Depending upon the type of metal selected and the diameter of such rod or wire stock, the slot 24 is formed, its depth and width determining the degree of pressural action applied by the coil 16 to the jaws 12 and 14 in biasing these jaws toward each other. In this way, a number of clips 10 can be initially identical with each other, yet the dimensions of the slot 24 selected so as to provide a desired amount of clamping force of the jaws 12 and 14 without applying a damaging amount of gripping force against the artery or vein being gripped.

When constructed in the manner just described, it will be appreciated that the U-shaped or humped portion 22 is guided by the sides of the slot 20 so that the jaws 12 and 14 are always maintained in alignment with each other. The alignment is achieved without resort to any component parts. Once again, it must be taken into account that an aneurysm clip is of small dimensions and that any need for plural parts or components make the clip more costly to manufacture. Of importance, too, is the possibility that any component parts might become inadvertently disassembled during actual use, an occurrence that must not be allowed to happen during an operation. Even if the parts become disassembled when not actually being used can pose a problem because loose parts can be lost, or even if retained the re-assembling is tedious because of the small size of clips of this type. Owing to the one-piece construction of our clip 10 the foregoing cannot occur.

We claim:

1. A one-piece aneurysm clip comprising first and second cooperable jaw portions, a resilient coil portion, a first connecting portion extending between said first jaw portion and said coil portion having a longitudinal slot therein, and a generally U-shaped second connecting portion extending between said second jaw portion and said coil portion, said second connecting portion being curved and having a thickness correlated with the width of said slot so as to be movable therein.

2. A one-piece aneurysm clip in accordance with claim 1 in which said second connecting portion includes a bight section.

3. A one-piece aneurysm clip in accordance with claim 2 in which said bight section projects beyond said first connecting portion when said jaw portions engage each other.

4. A one-piece aneurysm clip in accordance with claim 3 in which the greatest separation of said jaw portions achieved when the bight section is even with said first connecting portion.

* * * * *